United States Patent
Kamata

(10) Patent No.: US 8,610,180 B2
(45) Date of Patent: Dec. 17, 2013

(54) GAS SENSOR AND METHOD FOR MANUFACTURING THE GAS SENSOR

(75) Inventor: Koichiro Kamata, Isehara (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 309 days.

(21) Appl. No.: 13/154,692

(22) Filed: Jun. 7, 2011

(65) Prior Publication Data

US 2011/0303953 A1    Dec. 15, 2011

(30) Foreign Application Priority Data

Jun. 11, 2010    (JP) .................................. 2010-133916

(51) Int. Cl.
  *G01N 27/403*    (2006.01)
(52) U.S. Cl.
  USPC .................................. 257/253; 257/E29.296
(58) Field of Classification Search
  USPC .......................................... 257/253, E29.296
  See application file for complete search history.

(56) References Cited

U.S. PATENT DOCUMENTS

| | | | |
|---|---|---|---|
| 5,731,856 A | 3/1998 | Kim et al. | |
| 5,744,864 A | 4/1998 | Cillessen et al. | |
| 6,294,274 B1 | 9/2001 | Kawazoe et al. | |
| 6,563,174 B2 | 5/2003 | Kawasaki et al. | |
| 6,727,522 B1 | 4/2004 | Kawasaki et al. | |
| 7,049,190 B2 | 5/2006 | Takeda et al. | |
| 7,061,014 B2 | 6/2006 | Hosono et al. | |
| 7,064,346 B2 | 6/2006 | Kawasaki et al. | |
| 7,105,868 B2 | 9/2006 | Nause et al. | |
| 7,211,825 B2 | 5/2007 | Shih et al. | |
| 7,282,782 B2 | 10/2007 | Hoffman et al. | |
| 7,297,977 B2 | 11/2007 | Hoffman et al. | |
| 7,323,356 B2 | 1/2008 | Hosono et al. | |
| 7,385,224 B2 | 6/2008 | Ishii et al. | |
| 7,402,506 B2 | 7/2008 | Levy et al. | |

(Continued)

FOREIGN PATENT DOCUMENTS

| | | |
|---|---|---|
| EP | 1737044 A | 12/2006 |
| EP | 2226847 A | 9/2010 |

(Continued)

OTHER PUBLICATIONS

Fortunato.E et al., "Wide-Bandgap High-Mobility ZnO Thin-Film Transistors Produced at Room Temperature,", Appl. Phys. Lett. (Applied Physics Letters) , Sep. 27, 2004, vol. 85, No. 13, pp. 2541-2543.

(Continued)

*Primary Examiner* — Daniel Luke
(74) *Attorney, Agent, or Firm* — Eric J. Robinson; Robinson Intellectual Property Law Office, P.C.

(57) ABSTRACT

It is an object to provide a gas sensor which is formed by a simple manufacturing process. Another object is to provide a gas sensor whose manufacturing cost is reduced. A transistor which includes an oxide semiconductor layer in contact with a gas and which serves as a detector element of a gas sensor, and a transistor which includes an oxide semiconductor layer in contact with a film having a gas barrier property and which forms a detection circuit are formed over one substrate by the same process, whereby a gas sensor using these transistors may be formed.

8 Claims, 6 Drawing Sheets

(56) References Cited

U.S. PATENT DOCUMENTS

| | | | |
|---|---|---|---|
| 7,411,209 B2 | 8/2008 | Endo et al. | |
| 7,453,065 B2 | 11/2008 | Saito et al. | |
| 7,453,087 B2 | 11/2008 | Iwasaki | |
| 7,462,862 B2 | 12/2008 | Hoffman et al. | |
| 7,468,304 B2 | 12/2008 | Kaji et al. | |
| 7,501,293 B2 | 3/2009 | Ito et al. | |
| 7,674,650 B2 | 3/2010 | Akimoto et al. | |
| 7,732,819 B2 | 6/2010 | Akimoto et al. | |
| 2001/0046027 A1 | 11/2001 | Tai et al. | |
| 2002/0056838 A1 | 5/2002 | Ogawa | |
| 2002/0132454 A1 | 9/2002 | Ohtsu et al. | |
| 2003/0189401 A1 | 10/2003 | Kido et al. | |
| 2003/0218222 A1 | 11/2003 | Wager et al. | |
| 2004/0038446 A1 | 2/2004 | Takeda et al. | |
| 2004/0127038 A1 | 7/2004 | Carcia et al. | |
| 2005/0017302 A1 | 1/2005 | Hoffman | |
| 2005/0199959 A1 | 9/2005 | Chiang et al. | |
| 2006/0035452 A1 | 2/2006 | Carcia et al. | |
| 2006/0043377 A1 | 3/2006 | Hoffman et al. | |
| 2006/0091793 A1 | 5/2006 | Baude et al. | |
| 2006/0108529 A1 | 5/2006 | Saito et al. | |
| 2006/0108636 A1 | 5/2006 | Sano et al. | |
| 2006/0110867 A1 | 5/2006 | Yabuta et al. | |
| 2006/0113536 A1 | 6/2006 | Kumomi et al. | |
| 2006/0113539 A1 | 6/2006 | Sano et al. | |
| 2006/0113549 A1 | 6/2006 | Den et al. | |
| 2006/0113565 A1 | 6/2006 | Abe et al. | |
| 2006/0169973 A1 | 8/2006 | Isa et al. | |
| 2006/0170111 A1 | 8/2006 | Isa et al. | |
| 2006/0197092 A1 | 9/2006 | Hoffman et al. | |
| 2006/0208977 A1 | 9/2006 | Kimura | |
| 2006/0228974 A1 | 10/2006 | Thelss et al. | |
| 2006/0231882 A1 | 10/2006 | Kim et al. | |
| 2006/0238135 A1 | 10/2006 | Kimura | |
| 2006/0244107 A1 | 11/2006 | Sugihara et al. | |
| 2006/0284171 A1 | 12/2006 | Levy et al. | |
| 2006/0284172 A1 | 12/2006 | Ishii | |
| 2006/0292777 A1 | 12/2006 | Dunbar | |
| 2007/0024187 A1 | 2/2007 | Shin et al. | |
| 2007/0046191 A1 | 3/2007 | Saito | |
| 2007/0052025 A1 | 3/2007 | Yabuta | |
| 2007/0054507 A1 | 3/2007 | Kaji et al. | |
| 2007/0090365 A1 | 4/2007 | Hayashi et al. | |
| 2007/0108446 A1 | 5/2007 | Akimoto | |
| 2007/0152217 A1 | 7/2007 | Lai et al. | |
| 2007/0172591 A1 | 7/2007 | Seo et al. | |
| 2007/0187678 A1 | 8/2007 | Hirao et al. | |
| 2007/0187760 A1 | 8/2007 | Furuta et al. | |
| 2007/0194379 A1 | 8/2007 | Hosono et al. | |
| 2007/0252928 A1 | 11/2007 | Ito et al. | |
| 2007/0272922 A1 | 11/2007 | Kim et al. | |
| 2007/0287296 A1 | 12/2007 | Chang | |
| 2008/0006877 A1 | 1/2008 | Mardilovich et al. | |
| 2008/0038882 A1 | 2/2008 | Takechi et al. | |
| 2008/0038929 A1 | 2/2008 | Chang | |
| 2008/0050595 A1 | 2/2008 | Nakagawara et al. | |
| 2008/0073653 A1 | 3/2008 | Iwasaki | |
| 2008/0083950 A1 | 4/2008 | Pan et al. | |
| 2008/0106191 A1 | 5/2008 | Kawase | |
| 2008/0128689 A1 | 6/2008 | Lee et al. | |
| 2008/0129195 A1 | 6/2008 | Ishizaki et al. | |
| 2008/0166834 A1 | 7/2008 | Kim et al. | |
| 2008/0182358 A1 | 7/2008 | Cowdery-Corvan et al. | |
| 2008/0224133 A1 | 9/2008 | Park et al. | |
| 2008/0254569 A1 | 10/2008 | Hoffman et al. | |
| 2008/0257732 A1* | 10/2008 | Nakano et al. | 204/429 |
| 2008/0258139 A1 | 10/2008 | Ito et al. | |
| 2008/0258140 A1 | 10/2008 | Lee et al. | |
| 2008/0258141 A1 | 10/2008 | Park et al. | |
| 2008/0258143 A1 | 10/2008 | Kim et al. | |
| 2008/0296568 A1 | 12/2008 | Ryu et al. | |
| 2009/0068773 A1 | 3/2009 | Lai et al. | |
| 2009/0073325 A1 | 3/2009 | Kuwabara et al. | |
| 2009/0114910 A1 | 5/2009 | Chang | |
| 2009/0134399 A1 | 5/2009 | Sakakura et al. | |
| 2009/0152506 A1 | 6/2009 | Umeda et al. | |
| 2009/0152541 A1 | 6/2009 | Maekawa et al. | |
| 2009/0278122 A1 | 11/2009 | Hosono et al. | |
| 2009/0280600 A1 | 11/2009 | Hosono et al. | |
| 2010/0065844 A1 | 3/2010 | Tokunaga | |
| 2010/0092800 A1 | 4/2010 | Itagaki et al. | |
| 2010/0109002 A1 | 5/2010 | Itagaki et al. | |
| 2011/0113859 A1* | 5/2011 | Anthopoulos et al. | 73/31.06 |
| 2011/0180793 A1* | 7/2011 | Taniguchi | 257/43 |

FOREIGN PATENT DOCUMENTS

| | | |
|---|---|---|
| JP | 57-100714 | 6/1982 |
| JP | 59-147401 | 8/1984 |
| JP | 60-198861 A | 10/1985 |
| JP | 63-210022 A | 8/1988 |
| JP | 63-210023 A | 8/1988 |
| JP | 63-210024 A | 8/1988 |
| JP | 63-215519 A | 9/1988 |
| JP | 63-239117 A | 10/1988 |
| JP | 63-265818 A | 11/1988 |
| JP | 05-251705 A | 9/1993 |
| JP | 08-264794 A | 10/1996 |
| JP | 11-505377 | 5/1999 |
| JP | 2000-044236 A | 2/2000 |
| JP | 2000-150900 A | 5/2000 |
| JP | 2002-076356 A | 3/2002 |
| JP | 2002-289859 A | 10/2002 |
| JP | 2003-086000 A | 3/2003 |
| JP | 2003-086808 A | 3/2003 |
| JP | 2004-103957 A | 4/2004 |
| JP | 2004-273614 A | 9/2004 |
| JP | 2004-273732 A | 9/2004 |
| JP | 2006-165528 A | 6/2006 |
| WO | WO-2004/114391 | 12/2004 |

OTHER PUBLICATIONS

Dembo.H et al., "RFCPUS on Glass and Plastic Substrates Fabricated by TFT Transfer Technology,", IEDM 05: Technical Digest of International Electron Devices Meeting, Dec. 5, 2005, pp. 1067-1069.

Ikeda.T et al., "Full-Functional System Liquid Crystal Display Using CG-Silicon Technology,", SID Digest '04 : SID International Symposium Digest of Technical Papers, 2004, vol. 35, pp. 860-863.

Nomura.K et al., "Room-Temperature Fabrication of Transparent Flexible Thin-Film Transistors Using Amorphous Oxide Semiconductors,", Nature, Nov. 25, 2004, vol. 432, pp. 488-492.

Park.J et al., "Improvements in the Device Characteristics of Amorphous Indium Gallium Zinc Oxide Thin-Film Transistors by Ar Plasma Treatment,", Appl. Phys. Lett. (Applied Physics Letters) , Jun. 26, 2007, vol. 90, No. 26, pp. 262106-1-262106-3.

Takahashi.M et al., "Theoretical Analysis of IGZO Transparent Amorphous Oxide Semiconductor,", IDW '08 : Proceedings of the 15th International Display Workshops, Dec. 3, 2008, pp. 1637-1640.

Hayashi.R et al., "42.1: Invited Paper: Improved Amorphous In—Ga—Zn—O TFTS,", SID Digest '08 : SID International Symposium Digest of Technical Papers, May 20, 2008, vol. 39, pp. 621-624.

Prins.M et al., "A Ferroelectric Transparent Thin-Film Transistor,", Appl. Phys. Lett. (Applied Physics Letters) , Jun. 17, 1996, vol. 68, No. 25, pp. 3650-3652.

Nakamura.M et al., "The phase relations in the $In_2O_3$—$Ga_2ZnO_4$—ZnO system at 1350° C.,", Journal of Solid State Chemistry, Aug. 1, 1991, vol. 93, No. 2, pp. 298-315.

Kimizuka.N. et al., "Syntheses and Single-Crystal Data of Homologous Compounds, $In_2O_3(ZnO)m$ (m=3, 4, and 5), $InGaO_3(ZnO)3$, and $Ga_2O_3(ZnO)m$ (m=7, 8, 9, and 16) in the $In_2O_3$—$ZnGa_2O_4$—ZnO System,", Journal of Solid State Chemistry, Apr. 1, 1995, vol. 116, No. 1, pp. 170-178.

Nomura.K et al., "Thin-Film Transistor Fabricated in Single-Crystalline Transparent Oxide Semiconductor,", Science, May 23, 2003, vol. 300, No. 5623, pp. 1269-1272.

Masuda.S et al., "Transparent thin film transistors using ZnO as an active channel layer and their electrical properties,", J. Appl. Phys. (Journal of Applied Physics) , Feb. 1, 2003, vol. 93, No. 3, pp. 1624-1630.

(56) References Cited

OTHER PUBLICATIONS

Asakuma.N. et al., "Crystallization and Reduction of Sol-Gel-Derived Zinc Oxide Films by Irradiation With Ultraviolet Lamp,", Journal of Sol-Gel Science and Technology, 2003, vol. 26, pp. 181-184.

Osada.T et al., "15.2: Development of Driver-Integrated Panel using Amorphous In—Ga—Zn—Oxide TFT,", SID Digest '09 : SID International Symposium Digest of Technical Papers, May 31, 2009, pp. 184-187.

Nomura.K et al., "Carrier transport in transparent oxide semiconductor with intrinsic structural randomness probed using single-crystalline InGaO3(ZnO)5 films,", Appl. Phys. Lett. (Applied Physics Letters) , Sep. 13, 2004, vol. 85, No. 11, pp. 1993-1995.

Li.C et al., "Modulated Structures of Homologous Compounds InMO3(ZnO)m (M=In,Ga; m=Integer) Described by Four-Dimensional Superspace Group,", Journal of Solid State Chemistry, 1998, vol. 139, pp. 347-355.

Son.K et al., "42.4L: Late-News Paper: 4 Inch QVGA AMOLED Driven by the Threshold Voltage Controlled Amorphous GIZO (Ga2O3—In2O3—ZnO) TFT,", SID Digest '08 : SID International Symposium Digest of Technical Papers, May 20, 2008, vol. 39, pp. 633-636.

Lee.J. et al., "World's Largest (15-Inch) XGA AMLCD Panel Using IGZO Oxide TFT,", SID Digest '08 : SID International Symposium Digest of Technical Papers, May 20, 2008, vol. 39, pp. 625-628.

Nowatari.H et al., "60.2: Intermediate Connector With Suppressed Voltage Loss for White Tandem OLEDS,", SID Digest '09 : SID International Symposium Digest of Technical Papers, May 31, 2009, vol. 40, pp. 899-902.

Kanno.H et al., "White Stacked Electrophosphorecent Organic Light-Emitting Devices Employing MOO3 as a Charge-Generation Layer,", Adv. Mater. (Advanced Materials), 2006, vol. 18, No. 3, pp. 339-342.

Tsuda.K et al., "Ultra Low Power Consumption Technologies for Mobile TFT-LCDs ,", IDW '02 : Proceedings of the 9th International Display Workshops, Dec. 4, 2002, pp. 295-298.

Van de Walle.C, "Hydrogen as a Cause of Doping in Zinc Oxide,", Phys. Rev. Lett. (Physical Review Letters), Jul. 31, 2000, vol. 85, No. 5, pp. 1012-1015.

Fung.T et al., "2-D Numerical Simulation of High Performance Amorphous In—Ga—Zn—O TFTs for Flat Panel Displays,", AM-FPD '08 Digest of Technical Papers, Jul. 2, 2008, pp. 251-252, The Japan Society of Applied Physics.

Jeong.J et al., "3.1: Distinguished Paper: 12.1-Inch WXGA AMOLED Display Driven by Indium-Gallium-Zinc Oxide TFTs Array,", SID Digest '08 : SID International Symposium Digest of Technical Papers, May 20, 2008, vol. 39, No. 1, pp. 1-4.

Park.J et al., "High performance amorphous oxide thin film transistors with self-aligned top-gate structure,", IEDM 09: Technical Digest of International Electron Devices Meeting, Dec. 7, 2009, pp. 191-194.

Kurokawa.Y et al., "UHF RFCPUS on Flexible and Glass Substrates for Secure RFID Systems,", Journal of Solid-State Circuits, 2008, vol. 43, No. 1, pp. 292-299.

Ohara.H et al., "Amorphous In—Ga—Zn—Oxide TFTs with Suppressed Variation for 4.0 inch QVGA AMOLED Display,", AM-FPD '09 Digest of Technical Papers, Jul. 1, 2009, pp. 227-230, The Japan Society of Applied Physics.

Coates.D et al., "Optical Studies of the Amorphous Liquid-Cholesteric Liquid Crystal Transition:The "Blue Phase",", Physics Letters, Sep. 10, 1973, vol. 45A, No. 2, pp. 115-116.

Cho.D et al., "21.2:AL and SN-Doped Zinc Indium Oxide Thin Film Transistors for AMOLED Back-Plane,", SID Digest '09 : SID International Symposium Digest of Technical Papers, May 31, 2009, pp. 280-283.

Lee.M et al., "15.4:Excellent Performance of Indium-Oxide-Based Thin-Film Transistors by DC Sputtering,", SID Digest '09 : SID International Symposium Digest of Technical Papers, May 31, 2009, pp. 191-193.

Jin.D et al., "65.2:Distinguished Paper:World-Largest (6.5") Flexible Full Color Top Emission AMOLED Display on Plastic Film and Its Bending Properties,", SID Digest '09 : SID International Symposium Digest of Technical Papers, May 31, 2009, pp. 983-985.

Sakata.J et al., "Development of 4.0-In. AMOLED Display With Driver Circuit Using Amorphous In—Ga—Zn—Oxide TFTS,", IDW '09 : Proceedings of the 16th International Display Workshops, 2009, pp. 689-692.

Park.J et al., "Amorphous Indium-Gallium-Zinc Oxide TFTS and Their Application for Large Size AMOLED,", AM-FPD '08 Digest of Technical Papers, Jul. 2, 2008, pp. 275-278.

Park.S et al., "Challenge to Future Displays: Transparent AM-OLED Driven by Peald Grown ZnO TFT,", IMID '07 Digest, 2007, pp. 1249-1252.

Godo.H et al., "Temperature Dependence of Characteristics and Electronic Structure for Amorphous In—Ga—Zn—Oxide TFT,", AM-FPD '09 Digest of Technical Papers, Jul. 1, 2009, pp. 41-44.

Osada.T et al., "Development of Driver-Integrated Panel Using Amorphous In—Ga—Zn—Oxide TFT,", AM-FPD '09 Digest of Technical Papers, Jul. 1, 2009, pp. 33-36.

Hirao.T et al., "Novel Top-Gate Zinc Oxide Thin-Film Transistors (ZnO TFTS) for AMLCDS,", Journal of the SID, 2007, vol. 15, No. 1, pp. 17-22.

Hosono.H, "68.3:Invited Paper:Transparent Amorphous Oxide Semiconductors for High Performance TFT,", SID Digest '07 : SID International Symposium Digest of Technical Papers, 2007, vol. 38, pp. 1830-1833.

Godo.H et al., "P-9:Numerical Analysis on Temperature Dependence of Characteristics of Amorphous In—Ga—Zn—Oxide TFT,", SID Digest '09 : SID International Symposium Digest of Technical Papers, May 31, 2009, pp. 1110-1112.

Ohara.H et al., "21.3:4.0 In. QVGA AMOLED Display Using In—Ga—Zn—Oxide TFTS With a Novel Passivation Layer,", SID Digest '09 : SID International Symposium Digest of Technical Papers, May 31, 2009, pp. 284-287.

Miyasaka,M, "Suftla Flexible Microelectronics on Their Way to Business,", SID Digest '07 : SID International Symposium Digest of Technical Papers, 2007, vol. 38, pp. 1673-1676.

Chern.H et al., "An Analytical Model for the Above-Threshold Characteristics of Polysilicon Thin-Film Transistors,", IEEE Transactions on Electron Devices, Jul. 1, 1995, vol. 42, No. 7, pp. 1240-1246.

Kikuchi.H et al., "39.1:Invited Paper:Optically Isotropic Nano-Structured Liquid Crystal Composites for Display Applications,", SID Digest '09 : SID International Symposium Digest of Technical Papers, May 31, 2009, pp. 578-581.

Asaoka.Y et al., "29.1:Polarizer-Free Reflective LCD Combined With Ultra Low-Power Driving Technology,", SID Digest '09 : SID International Symposium Digest of Technical Papers, May 31, 2009, pp. 395-398.

Lee.H et al., "Current Status of, Challenges to, and Perspective View of AM-OLED ,", IDW '06 : Proceedings of the 13th International Display Workshops, Dec. 7, 2006, pp. 663-666.

Kikuchi.H et al., "62.2:Invited Paper:Fast Electro-Optical Switching in Polymer-Stabilized Liquid Crystalline Blue Phases for Display Application,", SID Digest '07 : SID International Symposium Digest of Technical Papers, 2007, vol. 38, pp. 1737-1740.

Nakamura.M, "Synthesis of Homologous Compound with New Long-Period Structure,", NIRIM Newsletter, Mar. 1, 1995, vol. 150, pp. 1-4.

Kikuchi.H et al., "Polymer-Stabilized Liquid Crystal Blue Phases,", Nature Materials, Sep. 1, 2002, vol. 1, pp. 64-68.

Kimizuka.N. et al., "Spinel,YBFE2O4, and YB2FE3O7 Types of Structures for Compounds in the IN2O3 and SC2O3—A2O3—BO Systems [A; Fe, Ga, or Al; B: Mg, Mn, Fe, Ni, Cu,or Zn] at Temperatures over 1000° C.,", Journal of Solid State Chemistry, 1985, vol. 60, pp. 382-384.

Kitzerow.H et al., "Observation of Blue Phases in Chiral Networks,", Liquid Crystals, 1993, vol. 14, No. 3, pp. 911-916.

Costello.M et al., "Electron Microscopy of a Cholesteric Liquid Crystal and Its Blue Phase,", Phys. Rev. A (Physical Review. A), May 1, 1984, vol. 29, No. 5, pp. 2957-2959.

Meiboom.S et al., "Theory of the Blue Phase of Cholesteric Liquid Crystals,", Phys. Rev. Lett. (Physical Review Letters), May 4, 1981, vol. 46, No. 18, pp. 1216-1219.

(56) References Cited

OTHER PUBLICATIONS

Park.Sang-Hee et al., "42.3: Transparent ZnO Thin Film Transistor for the Application of High Aperture Ratio Bottom Emission AM-OLED Display,", SID Digest '08 : SID International Symposium Digest of Technical Papers, May 20, 2008, vol. 39, pp. 629-632.

Orita.M et al., "Mechanism of Electrical Conductivity of Transparent InGaZnO4,", Phys. Rev. B (Physical Review. B), Jan. 15, 2000, vol. 61, No. 3, pp. 1811-1816.

Nomura.K et al., "Amorphous Oxide Semiconductors for High-Performance Flexible Thin-Film Transistors,", Jpn. J. Appl. Phys. (Japanese Journal of Applied Physics) , 2006, vol. 45, No. 5B, pp. 4303-4308.

Janotti.A et al., "Native Point Defects in ZnO,", Phys. Rev. B (Physical Review. B), Oct. 4, 2007, vol. 76, No. 16, pp. 165202-1-165202-22.

Park.J et al., "Electronic Transport Properties of Amorphous Indium-Gallium-Zinc Oxide Semiconductor Upon Exposure to Water,", Appl. Phys. Lett. (Applied Physics Letters) , 2008, vol. 92, pp. 072104-1-072104-3.

Hsieh.H et al., "P-29:Modeling of Amorphous Oxide Semiconductor Thin Film Transistors and Subgap Density of States,", SID Digest '08 : SID International Symposium Digest of Technical Papers, 2008, vol. 39, pp. 1277-1280.

Janotti.A et al., "Oxygen Vacancies in ZnO,", Appl. Phys. Lett. (Applied Physics Letters) , 2005, vol. 87, pp. 122102-1-122102-3.

Oba.F et al., "Defect energetics in ZnO: A hybrid Hartree-Fock density functional study,", Phys. Rev. B (Physical Review. B), 2008, vol. 77, pp. 245202-1-245202-6.

Orita.M et al., "Amorphous transparent conductive oxide InGaO3(ZnO)m (m<4):a Zn4s conductor,", Philosophical Magazine, 2001, vol. 81, No. 5, pp. 501-515.

Hosono.H et al., "Working hypothesis to explore novel wide band gap electrically conducting amorphous oxides and examples,", J. Non-Cryst. Solids (Journal of Non-Crystalline Solids), 1996, vol. 198-200, pp. 165-169.

Mo.Y et al., "Amorphous Oxide TFT Backplanes for Large Size AMOLED Displays,", IDW '08 : Proceedings of the 6th International Display Workshops, Dec. 3, 2008, pp. 581-584.

Kim.S et al., "High-Performance oxide thin film transistors passivated by various gas plasmas,", 214th ECS Meeting, 2008, No. 2317.

Clark.S et al., "First Principles Methods Using CASTEP,", Zeitschrift fur Kristallographie, 2005, vol. 220, pp. 567-570.

Lany.S et al., "Dopability, Intrinsic Conductivity, and Nonstoichiometry of Transparent Conducting Oxides,", Phys. Rev. Lett. (Physical Review Letters), Jan. 26, 2007, vol. 98, pp. 045501-1-045501-4.

Park.J et al., "Dry etching of ZnO films and plasma-induced damage to optical properties,", J. Vac. Sci. Technol. B (Journal of Vacuum Science & Technology B), Mar. 1, 2003, vol. 21, No. 2, pp. 800-803.

Oh.M et al., "Improving the Gate Stability of ZnO Thin-Film Transistors. With Aluminum Oxide Dielectric Layers,", J. Electrochem. Soc. (Journal of the Electrochemical Society), 2008, vol. 155, No. 12, pp. H1009-H1014.

Ueno.K et al., "Field-Effect Transistor on SrTiO3 With Sputtered Al2O3 Gate Insulator,", Appl. Phys. Lett. (Applied Physical Letters) , Sep. 1, 2003, vol. 83, No. 9, pp. 1755-1757.

\* cited by examiner

GAS SENSOR AND METHOD FOR MANUFACTURING THE GAS SENSOR

BACKGROUND OF THE INVENTION

1. Field of the Invention

The present invention relates to a gas sensor configured to detect a gas. The present invention relates to a method for manufacturing the gas sensor configured to detect a gas.

2. Description of the Related Art

A gas sensor configured to detect a gas in an atmosphere is used in various fields from household to industrial products, such as an air contamination monitor including a gas-leakage alarm or an air purifier, a function of automatic ventilation control of an automobile, and a breath analyzer.

A generally-known gas sensor is a resistant gas sensor using a resistance change due to an adsorption reaction or the like of a gas included in a metal oxide conductor.

A humidity sensor, which is one of gas sensors can detect moisture (water vapor) in an atmosphere and is used for a wide range of application from an air conditioning apparatus used for cooling and heating, humidification, dehumidification, and the like, a refrigerator, and a clothes dryer, to a weather reconnaissance aircraft, and a medical device.

Known humidity sensors are a resistant humidity sensor using a resistance change of metal or metal oxide conductor due to a difference in humidity (Patent Document 1), a capacitive humidity sensor using a permittivity change of an insulating film provided between electrodes (Patent Document 2), and the like.

A gas sensor generally has a structure in which a detection portion where electrical characteristics (e.g., electric resistance or permittivity) are changed by the gas adsorption action or the like and a circuit portion that converts the change of the electrical characteristics into an electrical signal (e.g., voltage change) and outputs the electrical signal are combined.

On the other hand, a technique in which a semiconductor device is formed using a semiconductor film formed over a substrate is known. For example, a technique in which a transistor is formed over a glass substrate using a thin film containing a silicon-based semiconductor material is known.

Amorphous silicon, polycrystalline silicon, and the like are known as semiconductor materials. Although transistors including amorphous silicon have low field effect mobility, a larger substrate can be used in the case of using amorphous silicon. Meanwhile, although transistors including polycrystalline silicon have high field-effect mobility, they need to be subjected to a crystallization step such as laser annealing and have characteristics such that they are not always suitable for larger substrates.

As another material, an oxide semiconductor has attracted attention recently. For example, a transistor whose active layer includes an amorphous oxide containing indium (In), gallium (Ga), and zinc (Zn) and having an electron carrier concentration of less than $10^{18}/cm^3$ is disclosed (see Patent Document 3).

REFERENCE

[Patent Document 1] Japanese Published Patent Application No. S59-147401
[Patent Document 2] Japanese Published Patent Application No. S57-100714
[Patent Document 3] Japanese Published Patent Application No. 2006-165528

SUMMARY OF THE INVENTION

In a conventional gas sensor, a detection portion and a circuit portion are formed using different materials; therefore, the detection portion and the circuit portion need to be formed by different manufacturing steps. Accordingly, there is a problem in that a manufacturing process is complicated and manufacturing cost is high.

Thus, an object of the present invention is to provide a gas sensor which is formed by a simple manufacturing process. Another object is to provide a gas sensor whose manufacturing cost is reduced.

To achieve the above-described objects, a thin film transistor whose semiconductor layer includes an oxide semiconductor is thought to be used as a detector element of a gas sensor.

It is found that electrical characteristics of a transistor including an oxide semiconductor layer in contact with a gas in an atmosphere are changed due to gas concentration in the atmosphere, and that a transistor including an oxide semiconductor layer in contact with a film having a gas barrier property has electrical characteristics and superior reliability regardless of the gas concentration in the atmosphere. The transistor including the oxide semiconductor layer in contact with the gas in the atmosphere is used as a detector element, a detection circuit is formed using the transistor including the oxide semiconductor layer in contact with the film having a gas barrier property, and a gas sensor is provided with the detector element and the detection circuit over one substrate of one embodiment of the present invention, whereby the problem is solved.

In the present invention, an oxide semiconductor layer of a transistor serving as a detector element is in contact with a gas in an atmosphere. Thus, a change in electrical characteristics of the transistor due to the gas in the atmosphere is utilized, whereby the gas can be detected.

An oxide semiconductor layer of a transistor included in a detection circuit is in contact with a film having a gas barrier property. Thus, the detection circuit which is superior in reliability can be formed without an effect of the gas in the atmosphere.

Two kinds of transistors included in the detector element and the detection circuit are formed over one substrate by the same process, whereby a gas sensor can be formed at low cost without a complicated manufacturing process.

Therefore, to solve the above-described problem, a transistor which includes an oxide semiconductor layer in contact with a gas and which serves as a detector element of a gas sensor, and a transistor which includes an oxide semiconductor layer in contact with a film having a gas barrier property and which forms a detection circuit are formed over one substrate by the same process, whereby a gas sensor using these transistors may be formed.

In other words, one embodiment of the present invention is a gas sensor that includes a detection portion including a first transistor and a circuit portion including a second transistor over one insulating surface. The first transistor includes a first gate electrode layer over the insulating surface; a gate insulating layer over the first gate electrode layer; and a first oxide semiconductor layer one surface of which is in contact with the gate insulating layer and the other surface of which is in contact with an atmosphere, which overlaps with the first gate electrode layer. The first transistor includes a first source electrode layer and a first drain electrode layer that are in contact with the first oxide semiconductor layer and that are not provided in a portion overlapping with the first gate electrode layer. The second transistor includes a second gate electrode layer over the insulating surface; the gate insulating layer over the second gate electrode layer; a second oxide semiconductor layer one surface of which is in contact with the gate insulating layer and the other surface of which is in contact with a protective insulating layer, which overlaps with the second gate electrode layer; and a second source electrode layer and a second drain electrode layer that are in contact with the second oxide semiconductor layer and that are not provided in a portion overlapping with the second gate electrode layer.

The gas sensor according to one embodiment of the present invention includes a transistor serving as a detector element and a transistor included in a detection circuit over one surface. Two kinds of transistors are formed over one surface, whereby the gas sensor can be achieved at low cost. The oxide semiconductor layer of the detector element is exposed to an atmosphere to be measured; therefore, a gas sensor with high detection sensitivity can be achieved.

One embodiment of the present invention is the gas sensor, in which an insulating layer including a gas permeable property is in contact with the atmosphere and provided between the first oxide semiconductor layer and the atmosphere.

An insulating layer is provided between the oxide semiconductor layer of the transistor serving as a detector element and the atmosphere to be measured, whereby a highly reliable gas sensor in which unintended contamination from the atmosphere to be measured can be reduced can be provided.

One embodiment of the present invention is a method for forming a gas sensor, in which a first gate electrode layer and a second gate electrode layer are formed over an insulating surface, and a gate insulating layer is formed over the first gate electrode layer and the second gate electrode layer. Over the gate insulating layer, a first oxide semiconductor layer overlapping with the first gate electrode layer, a second oxide semiconductor layer overlapping with the second gate electrode layer, a first source electrode layer and a first drain electrode layer that are in contact with the first oxide semiconductor layer and that are not provided in a portion overlapping with the first gate electrode layer, and a second source electrode layer and a second drain electrode layer that are in contact with the second oxide semiconductor layer and that are not provided in a portion overlapping with the second gate electrode layer are formed. Then, a protective insulating layer in contact with an exposed portion of the second oxide semiconductor layer is formed.

The gas sensor is formed by the above-described method, whereby the transistor included in the detection portion and the transistor included in the circuit portion can be formed through the same manufacturing process at the same time. Accordingly, a manufacturing process can be simplified, and the gas sensor can be formed at low cost. Further, the oxide semiconductor layer of the detector element is exposed to the atmosphere to be measured; therefore, a gas sensor with high detection sensitivity can be formed.

One embodiment of the present invention is a method for manufacturing the gas sensor, which includes the step of forming an insulating layer including a gas permeable property which is in contact with an atmosphere and is over a first oxide semiconductor layer after the protective insulating layer is formed.

The gas sensor is formed by the above-described method, whereby the oxide semiconductor layer of the transistor serving as a detector element can be protected by the insulating layer, unintended contamination from the atmosphere to be measured can be reduced, and a highly reliable gas sensor can be formed.

According to the present invention, a gas sensor with a simple manufacturing process can be provided. Further, a gas sensor with low manufacturing cost can be provided.

DETAILED DESCRIPTION OF THE INVENTION

Figure 1A:
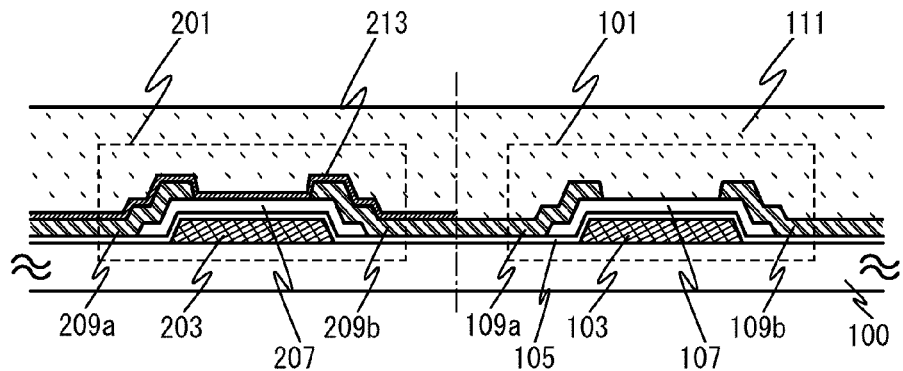
FIGS. 1A to 1C each illustrate a gas sensor according to one embodiment of the present invention.

Embodiments and examples will be described in detail with reference to drawings. Note that the present invention is not limited to the following description, and it will be easily understood by those skilled in the art that various changes and modifications can be made without departing from the spirit and scope of the invention. Therefore, the present invention should not be construed as being limited to the description in the following embodiments and examples. Note that in the structures of the present invention described below, the same portions or portions having similar functions are denoted by the same reference numerals in different drawings, and description of such portions is not repeated.

Note that in each drawing described in this specification, the size, the layer thickness, or the region of each component is exaggerated for clarity in some cases. Therefore, embodiments and examples of the present invention are not limited to such scales.

Embodiment 1

In this embodiment, an example of a humidity sensor which is one of gas sensors will be described. One embodiment of a structure of the humidity sensor using a thin film transistor whose semiconductor layer includes an oxide semiconductor and a method for manufacturing the humidity sensor will be described with reference to FIGS. 1A to 1C and FIGS. 2A to 2E.

FIG. 1A is a schematic cross-sectional view of a thin film transistor 101 serving as a detector element and a thin film transistor 201 included in a detection circuit which are formed over one substrate in a humidity sensor.

The thin film transistor 101 and the thin film transistor 201 each have a bottom-gate structure called a top-contact type (also referred to as an inverted staggered type). Further, the thin film transistor 101 and the thin film transistor 201 are each an n-channel transistor.

The thin film transistor 101 includes, over a substrate 100, a gate electrode layer 103, a gate insulating layer 105, an oxide semiconductor layer 107, a source electrode layer 109a, and a drain electrode layer 109b. Further, a back channel of the oxide semiconductor layer 107 is in contact with an insulating layer 111.

Here, in a bottom-gate transistor, a region of an oxide semiconductor layer, which overlaps with a gate electrode layer and which is provided between end portions of a source electrode layer and a drain electrode layer that are paired and face each other, is called a channel formation region. Further, a surface of the channel formation region, which is opposite to a surface facing the gate electrode layer, is called a back channel.

The thin film transistor 201 has the same structure as the thin film transistor 101 except that a source electrode layer 209a, a drain electrode layer 209b, and a back channel of an oxide semiconductor layer 207 are in contact with a protective insulating layer 213. Therefore, a gate electrode layer 203, the gate insulating layer 105, the oxide semiconductor layer 207, the source electrode layer 209a, and the drain electrode layer 209b are formed using the same material and the same process as those of the thin film transistor 101.

A water-absorbing material is used for the insulating layer 111 in contact with the back channel of the thin film transistor 101 serving as the detector element. Therefore, the insulating layer 111 absorbs a given amount of water vapor which is dependent on humidity of an atmosphere to be measured. Since the insulating layer 111 is in contact with the back channel of the thin film transistor 101, water vapor absorbed by the insulating layer 111 is in contact with the channel formation region of the oxide semiconductor layer 107, whereby electrical characteristics are changed. Specifically, when moisture is in contact with or enters the oxide semiconductor layer 107, carriers in the semiconductor layer are increased. Since the thin film transistor 101 is an n-channel transistor, the increase in the carriers in the semiconductor layer is observed as a decrease in threshold voltage of the thin film transistor 101. In other words, a value of the threshold voltage of the thin film transistor 101 is determined by humidity in the atmosphere to be measured; therefore, the humidity in the atmosphere to be measured can be obtained from the value of the threshold voltage.

The back channel of the thin film transistor 101 is covered with the insulating layer 111 having a water-absorbing property, whereby an effect such as unintended contamination on the back channel can be reduced; therefore, a humidity sensor with less variation in characteristics due to repeated use and with high reliability can be formed.

In contrast, an inorganic insulating film without water-absorbing property is used for the protective insulating layer 213 in contact with the back channel of the thin film transistor 201 included in the detection circuit. Therefore, even when the insulating layer 111 absorbs water vapor, electrical characteristics of the channel formation region of the oxide semiconductor layer 207 in contact with the protective insulating layer 213 remain unchanged because the back channel of the thin film transistor 201 is protected by the protective insulating layer 213. Therefore, when the protective insulating layer 213 is provided, the thin film transistor 201 with high reliability and with less variation in electrical characteristics with respect to humidity can be provided.

With such a structure, the thin film transistor 101 serving as the detector element used to detect humidity and the thin film transistor 201 included in the detection circuit can be formed over one substrate.

Steps for manufacturing the thin film transistor 101 and the thin film transistor 201 over one substrate will be described below with reference to FIGS. 2A to 2E.

First, a conductive layer is formed over the substrate 100 having an insulating surface; then, the gate electrode layer 103 and the gate electrode layer 203 are formed in a first photolithography step.

A resist mask used for forming the gate electrode layer 103 and the gate electrode layer 203 may be formed by an inkjet method. Formation of the resist mask by an inkjet method needs no photomask; thus, manufacturing cost can be reduced.

There is no particular limitation on the substrate 100 as long as the substrate 100 has an insulating surface; it is necessary that the substrate 100 have at least enough heat resistance to withstand heat treatment in the case where the heat treatment is to be performed in a later step. For example, a glass substrate of barium borosilicate glass, aluminoborosilicate glass, or the like, a quartz substrate, a sapphire substrate, a ceramic substrate, or the like may be used. Alternatively, a metal substrate containing stainless steel or a semiconductor substrate having an insulating film formed on its surface can be used. There is a tendency that a flexible substrate formed using a synthetic resin such as plastics generally has a lower upper temperature limit than the above substrates; however, such a substrate can be used as long as it can withstand processing temperature in manufacturing steps. Note that the surface of the substrate 100 may be planarized by polishing such as a CMP method.

A conductive layer which serves as the gate electrode layer 103 and the gate electrode layer 203 can be formed to have a single layer or a stacked layer using a metal material such as molybdenum, titanium, chromium, tantalum, tungsten, aluminum, copper, neodymium, or scandium, or an alloy material which contains any of these materials as a main component.

In this embodiment, a tungsten film with a thickness of 150 nm is formed by a sputtering method as the conductive layer which serves as the gate electrode layer 103 and the gate electrode layer 203.

Note that an insulating film serving as a base layer may be formed between the substrate 100, and the gate electrode layer 103 and the gate electrode layer 203. The base layer has a function of preventing diffusion of an impurity element from the substrate 100, and can be formed to have a single-layer or layered structure using one or more of a silicon nitride film, a silicon oxide film, a silicon nitride oxide film, and a silicon oxynitride film.

As the insulating film serving as a base, it is further preferable to employ a layered structure of an insulating film containing a material different from that of an oxide semiconductor film to be formed later and an insulating film formed using an insulating material containing a constituent similar to that of the oxide semiconductor film. For example, a layered structure of a gallium oxide film and a silicon oxide film, a layered structure of a gallium oxide film and a silicon nitride film, or the like may be used.

Next, the gate insulating layer 105 is formed so as to cover the gate electrode layer 103, the gate electrode layer 203, and an exposed portion of the substrate. In this embodiment, a silicon oxide film is formed to have a thickness of 30 nm by a sputtering method.

In this embodiment, the gate insulating layer 105 is formed to have a single-layer structure of a silicon oxide film; however, the gate insulating layer is not limited thereto. The gate insulating layer can have a single-layer or layered structure including a silicon nitride film, a silicon oxynitride film, a silicon nitride oxide film, an aluminum oxide film, or the like. An oxide insulating film is preferably used as a layer in contact with the oxide semiconductor layer. The gate insulating layer can be formed by a plasma-enhanced CVD method, a sputtering method, or the like. In order to prevent the gate insulating layer from containing a large amount of hydrogen, the gate insulating layer is preferably deposited by a sputtering method. There is no particular limitation on the thickness of the gate insulating layer; the thickness can be greater than or equal to 10 nm and less than or equal to 500 nm, for example.

Figure 2A:
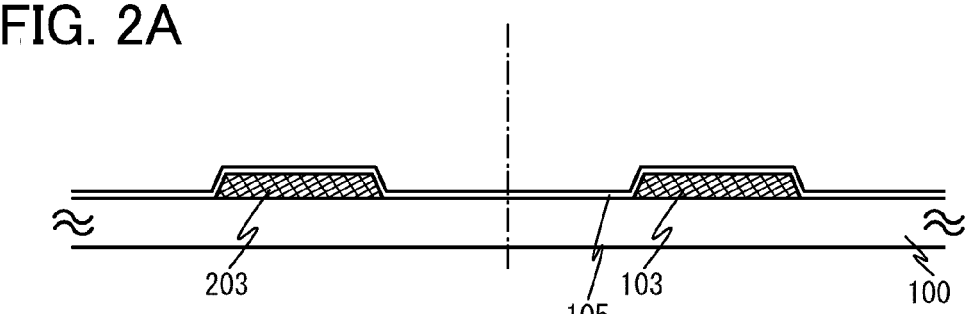
FIGS. 2A to 2E illustrate a method for manufacturing a gas sensor, according to one embodiment of the present invention.

FIG. 2A illustrates a schematic cross-sectional view at this stage.

Next, the oxide semiconductor layer 107 and the oxide semiconductor layer 207 are formed.

As a material used for the oxide semiconductor layer 107 and the oxide semiconductor layer 207, an In—Sn—Ga—Zn—O-based oxide semiconductor which is a quaternary metal oxide; an In—Ga—Zn—O-based oxide semiconductor, an In—Sn—Zn—O-based oxide semiconductor, an In—Al—Zn—O-based oxide semiconductor, a Sn—Ga—Zn—O-based oxide semiconductor, an Al—Ga—Zn—O-based oxide semiconductor, or a Sn—Al—Zn—O-based oxide semiconductor which is a ternary metal oxide; an In—Zn—O-based oxide semiconductor, a Sn—Zn—O-based oxide semiconductor, an Al—Zn—O-based oxide semiconductor, a Zn—Mg—O-based oxide semiconductor, a Sn—Mg—O-based oxide semiconductor, an In—Mg—O-based oxide semiconductor, or an In—Ga—O-based oxide semiconductor which is a binary metal oxide; or an In—O-based oxide semiconductor, a Sn—O-based oxide semiconductor, or a Zn—O-based oxide semiconductor can be used. In addition, any of the above oxide semiconductors may contain an element other than In, Ga, Sn, and Zn, for example, $SiO_2$. Here, for example, an In—Ga—Zn—O-based oxide semiconductor means an oxide containing at least indium (In), gallium (Ga), and zinc (Zn), and there is no particular limitation on the composition ratio thereof. Further, the In—Ga—Zn—O-based oxide semiconductor may contain an element other than In, Ga, and Zn.

The oxide semiconductor film is non-single-crystal and the oxide semiconductor film is not entirely in an amorphous state. Since the oxide semiconductor film is not entirely in an amorphous state, formation of an amorphous portion whose electrical characteristics are unstable is suppressed. At least part of a region of the oxide semiconductor film may have crystallinity, be non-single-crystal, have atoms arranged in a triangular, hexagonal, equilateral triangular, or regular hexagonal shape when seen from a direction perpendicular to an a-b plane, and have a phase in which metal atoms are arranged in layers in the c-axis direction or a phase in which metal atoms and oxygen atoms are arranged in layers in the c-axis direction.

Each of the oxide semiconductor layer 107 and the oxide semiconductor layer 207 may be a thin film formed using a material represented by the chemical formula, $InMO_3(ZnO)_m$ (m>0). Here, M represents one or more metal elements selected from Ga, Al, Mn, and Co. For example, M can be Ga, Ga and Al, Ga and Mn, Ga and Co, or the like.

In the case where an In—Zn—O-based material is used for the oxide semiconductor, a target used has a composition ratio of In:Zn=50:1 to 1:2 in an atomic ratio ($In_2O_3$:ZnO=25:1 to 1:4 in a molar ratio), preferably In:Zn=20:1 to 1:1 in an atomic ratio ($In_2O_3$:ZnO=10:1 to 2:1 in a molar ratio), further preferably In:Zn=15:1 to 1.5:1 ($In_2O_3$:ZnO=15:2 to 3:4 in a molar ratio). For example, in a target used for formation of an In—Zn—O-based oxide semiconductor which has an atomic ratio of In:Zn:O=X:Y:Z, the relation of Z>1.5X+Y is satisfied.

The oxide semiconductor layer 107 and the oxide semiconductor layer 207 can be formed by a sputtering method in a rare gas (typically argon) atmosphere, an oxygen atmosphere, or a mixed atmosphere of a rare gas and oxygen. As the gas at this time, it is preferable to use a high-purity gas from which an impurity such as hydrogen, water, a hydroxyl group, or hydride is removed.

In this embodiment, the oxide semiconductor film used for the oxide semiconductor layer 107 and the oxide semiconductor layer 207 is formed to have a thickness of 100 nm by a sputtering method with the use of an In—Ga—Zn—O-based oxide semiconductor target.

Before the oxide semiconductor film is formed, heat treatment (at higher than or equal to 400° C. and lower than the strain point of the substrate) may be performed in an atmosphere of an inert gas (e.g., nitrogen, helium, neon, or argon) so that impurities such as hydrogen and water, which are included in the gate insulating layer, are removed.

Figure 2B:
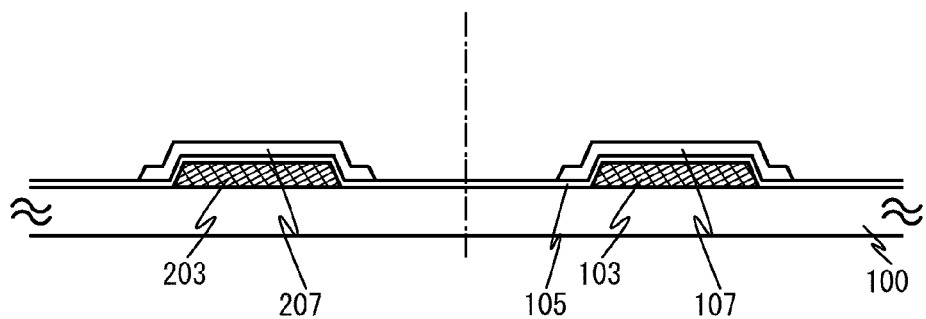

After the oxide semiconductor film is formed, the oxide semiconductor layer 107 and the oxide semiconductor layer 207 are formed in a second photolithography step. FIG. 2B illustrates a schematic cross-sectional view at this stage.

A resist mask used for forming the oxide semiconductor layer 107 and the oxide semiconductor layer 207 may be formed by an inkjet method. Formation of the resist mask by an inkjet method needs no photomask; thus, manufacturing cost can be reduced.

After the oxide semiconductor layer 107 and the oxide semiconductor layer 207 are formed, first heat treatment may be performed. Excessive water (including a hydroxyl group), hydrogen, or the like contained in the oxide semiconductor layer 107 and the oxide semiconductor layer 207 can be removed by the first heat treatment. The temperature of the first heat treatment is higher than or equal to 350° C. and lower than the strain point of the substrate, preferably higher than or equal to 400° C. and lower than the strain point of the substrate.

The oxide semiconductor layer 107 and the oxide semiconductor layer 207 can be dehydrated or dehydrogenated when the first heat treatment is performed at a temperature of 350° C. or higher, so that the concentration of hydrogen in the oxide semiconductor layers can be reduced. The first heat treatment at a temperature of 450° C. or higher allows a further reduction in the hydrogen concentration in the layers. The first heat treatment at a temperature of 550° C. or higher allows a still further reduction in the hydrogen concentration in the layers.

As the atmosphere in which the first heat treatment is performed, it is preferable to employ an inert gas that contains nitrogen or a rare gas (e.g., helium, neon, or argon) as a main component and does not contain water, hydrogen, or the like. For example, the purity of the gas introduced to a heat treatment apparatus can be 6N (99.9999%) or more, preferably 7N (99.99999%) or more. In this manner, the oxide semiconductor layer 107 and the oxide semiconductor layer 207 are not exposed to the air during the first heat treatment so that the entry of water or hydrogen can be prevented.

The apparatus for the heat treatment is not limited to the electric furnace and may be the one provided with a device for heating an object to be processed, using heat conduction or heat radiation from a heating element such as a resistance heating element. For example, a rapid thermal anneal (RTA) apparatus such as a gas rapid thermal anneal (GRTA) apparatus or a lamp rapid thermal anneal (LRTA) apparatus can be used. An LRTA apparatus is an apparatus for heating an object to be processed by radiation of light (an electromagnetic wave) emitted from a lamp such as a halogen lamp, a metal halide lamp, a xenon arc lamp, a carbon arc lamp, a high pressure sodium lamp, or a high pressure mercury lamp. A GRTA apparatus is an apparatus for performing heat treatment using a high-temperature gas. An inert gas which does not react with an object to be processed by heat treatment, nitrogen or a rare gas (e.g., argon), is used as the gas.

In this embodiment, as the first heat treatment, heat treatment is performed at 650° C. for six minutes in a nitrogen atmosphere with the use of a GRTA apparatus.

Next, the source electrode layer 109a, the drain electrode layer 109b, the source electrode layer 209a, and the drain electrode layer 209b (hereinafter these layers are collectively referred to as SD electrode layers) are formed.

Further, as a material for the SD electrode layers, an element selected from Al, Cr, Cu, Ta, Ti, Mo, and W, an alloy containing any of the above elements as a component, an alloy containing any of the above elements in combination, or the like can be used, for example. Further, a structure may be employed in which a high-melting-point metal film of Ti film, Mo film, W film, or the like is formed on one or both of a top surface and a bottom surface of a metal film of Al film, Cu film, or the like. When an Al material to which an element (e.g., Si, Nd, or Sc) which prevents generation of hillocks and whiskers in an Al film is added is used, heat resistance can be increased. The SD electrode layers may be formed using a conductive metal oxide. As the conductive metal oxide, indium oxide ($In_2O_3$), tin oxide ($SnO_2$), zinc oxide (ZnO), indium oxide-tin oxide alloy ($In_2O_3$—$SnO_2$, which is abbreviated to ITO), indium oxide-zinc oxide alloy ($In_2O_3$—ZnO), or any of these metal oxide materials in which silicon oxide is contained can be used.

In this embodiment, as a conductive film used for the SD electrode, a Ti film with a thickness of 150 nm is formed by a sputtering method.

Next, the source electrode layer 109a, the drain electrode layer 109b, the source electrode layer 209a, and the drain electrode layer 209b are formed in a third photolithography step.

A resist mask used for forming the source electrode layer 109a, the drain electrode layer 109b, the source electrode layer 209a, and the drain electrode layer 209b may be formed by an inkjet method. Formation of the resist mask by an inkjet method needs no photomask; thus, manufacturing cost can be reduced.

Note that it is preferable that etching conditions be optimized so as not to etch and divide exposed portions of the oxide semiconductor layer 107 and the oxide semiconductor layer 207 when the conductive layer is etched. However, it is difficult to obtain etching conditions in which only the conductive layer is etched and the oxide semiconductor layer 107 and the oxide semiconductor layer 207 are not etched at all. In some cases, only parts of the oxide semiconductor layer 107 and the oxide semiconductor layer 207 are etched to be the oxide semiconductor layer 107 and the oxide semiconductor layer 207 each having a groove portion (a recessed portion) when the conductive layer is etched.

Figure 2C:
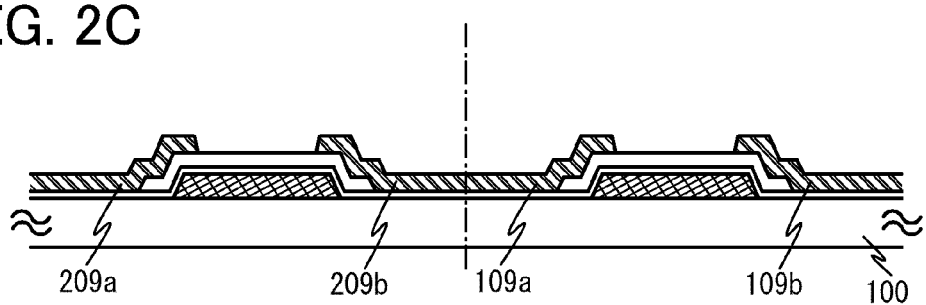

FIG. 2C illustrates a schematic cross-sectional view at this stage.

Next, the protective insulating layer 213 in contact with the back channel of the thin film transistor included in the detection circuit is formed.

A film that rarely allows permeation of moisture can be used for the protective insulating layer 213. For example, a silicon nitride film or the like can be used. The protective insulating layer 213 can be formed by a sputtering method, so that a dense film that rarely allows permeation of moisture can be obtained.

Since the protective insulating layer 213 is in contact with the oxide semiconductor layer 207, it is important that a deposition method in which hydrogen is not used be employed in order to form the protective insulating layer 213 containing as little hydrogen as possible. When hydrogen is included in the protective insulating layer 213, entry of hydrogen to the oxide semiconductor layer 207 or extraction of oxygen in the oxide semiconductor layer 207 by the hydrogen is caused; thus, a backchannel of the oxide semiconductor layer 207 comes to have low resistance, whereby a parasitic channel might be formed.

A film of the protective insulating layer 213 in contact with the oxide semiconductor layer 207 is preferably formed using an oxide insulating film. The protective insulating layer 213 is formed using an oxide insulating film with reduced hydrogen concentration, whereby oxygen is supplied from the protective insulating layer 213 to defects in the oxide semiconductor layer 207; accordingly, a transistor has good electrical characteristics. Therefore, the protective insulating layer 213 is preferably formed using a layered film of an oxide insulating film and a silicon nitride film.

In this embodiment, as an insulating film used for the protective insulating layer 213, a silicon oxide film with a thickness of 20 nm and a silicon nitride film with a thickness of 20 nm are stacked by a sputtering method.

Figure 2D:
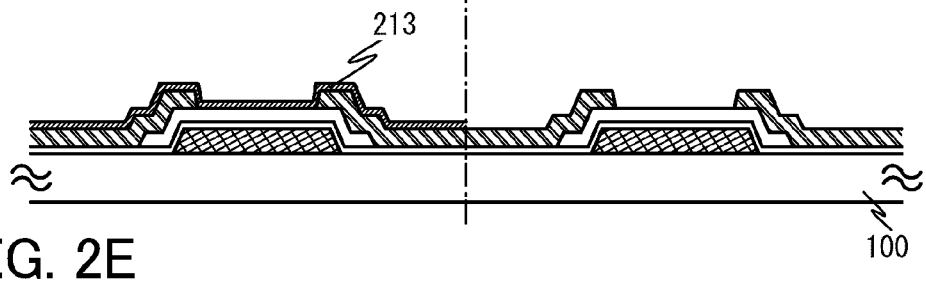

Then, the protective insulating layer 213 is formed in a fourth photolithography step. FIG. 2D illustrates a schematic cross-sectional view at this stage.

A resist mask used for forming the protective insulating layer 213 may be formed by an inkjet method. Formation of the resist mask by an inkjet method needs no photomask; thus, manufacturing cost can be reduced.

The second heat treatment may be performed after formation of the protective insulating layer 213. The temperature of the second heat treatment may be set as appropriate in consideration of heat resistance of a conductive material used for the SD electrode layers.

Next, the insulating layer 111 having a water-absorbing property is formed to be in contact with the oxide semiconductor layer 107.

As the insulating layer 111 having a water-absorbing property, a film which absorbs moisture due to the humidity in the atmosphere to be measured can be used. Preferably, a film whose water absorption rate is 3% or more can be used. For example, an organic resin film such as polyimide, acrylic, or a siloxane-based resin can be used.

In this embodiment, as the insulating layer 111, a 1-μm-thick polyimide film such that polyimide is applied by spin coating and baked at 300° C. to be thermally polymerized is used.

Note that there is no particular limitation on the formation method of the insulating layer 111, and the following method can be employed depending on the material: a method such as spin coating, dip coating, spray coating, or a droplet discharge method (e.g., an ink jet method, screen printing, or offset printing), or with a tool (equipment) such as a roll coater, a curtain coater, or a knife coater.

Note that although the insulating layer 111 having a water-absorbing property is in contact with the oxide semiconductor layer 107 in this embodiment, a space may be provided between the insulating layer 111 and the oxide semiconductor layer 107.

Figure 2E:
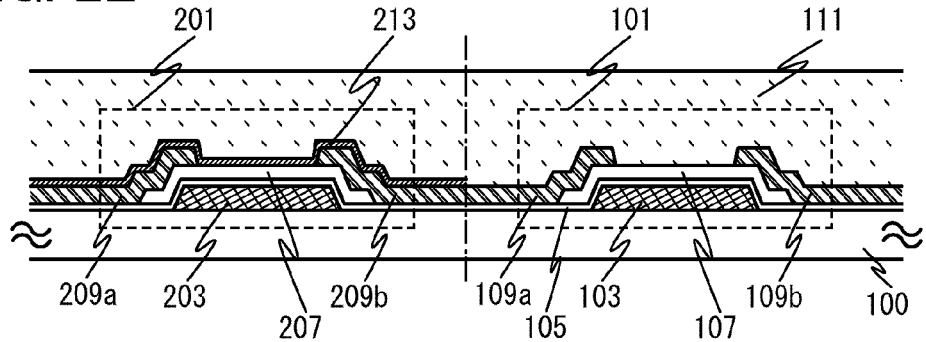

Through the above process, the thin film transistor 101 serving as the detector element and the thin film transistor 201 included in the detection circuit can be formed over one substrate in the humidity sensor. FIG. 2E illustrates a schematic cross-sectional view at this stage. Note that FIG. 2E is the same view as FIG. 1A.

Figure 1B:
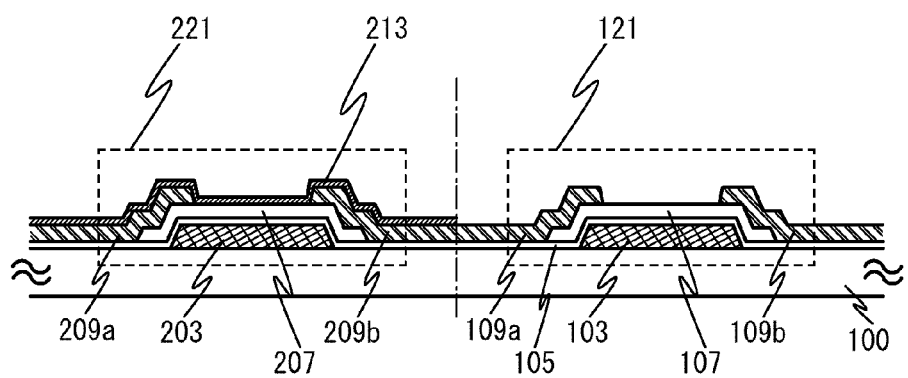

Note that as illustrated in FIG. 1B, a thin film transistor 121 and a thin film transistor 221 without the insulating layer 111 having a water-absorbing property may be used. In this case, a back channel of the thin film transistor 121 serving as a detector element is exposed to the atmosphere to be measured. In this case, a change of the humidity in the atmosphere to be measured can be detected sensitively; therefore, the response speed can be increased and the detection sensitivity can be further increased.

Figure 1C:
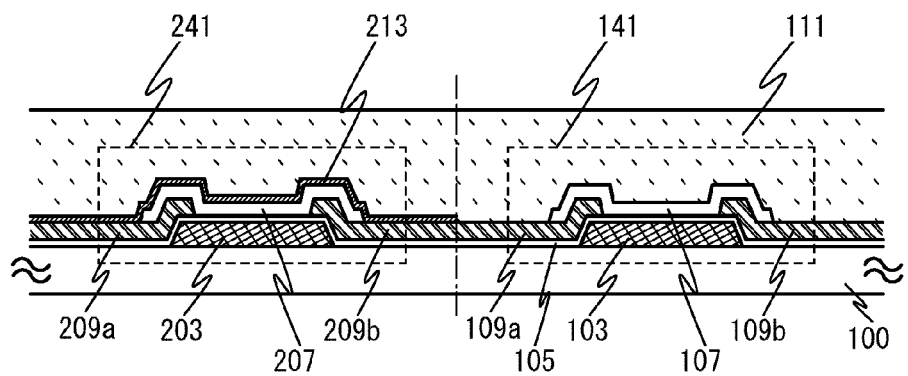

Note that although a top-contact thin film transistor is formed in this embodiment, a bottom-contact thin film transistor as illustrated in FIG. 1C may be used. After the gate insulating layer 105 is formed, the source electrode layer 109a, the drain electrode layer 109b, the source electrode layer 209a, and the drain electrode layer 209b are formed; then, the oxide semiconductor layer 107 and the oxide semiconductor layer 207 are formed, whereby a thin film transistor 141 and a thin film transistor 241 may be formed. The oxide semiconductor layers are formed after the source electrode layers and the drain electrode layers are formed in this way, whereby film reduction of the oxide semiconductor layers can be prevented when the source electrode layers and the drain electrode layers are etched, and a thin film transistor with higher reliability can be provided.

Although not illustrated, even in the case where the above-described bottom-contact thin film transistor is used, a structure without the insulating layer 111 having a water-absorbing property may be used. Also in this case, a humidity sensor with high response speed and higher detection sensitivity as described above can be formed.

Note that although the structure of the humidity sensor which is one of gas sensors is described in this embodiment, a gas sensor according to one embodiment of the present invention can detect a highly reactive gas such as hydrogen, carbon monoxide, alcohol, chlorine, chlorofluorocarbon, ammonia, ozone, or hydrogen sulfide.

In the case where the above-described gas is detected, a structure in which a back channel of a thin film transistor serving as a detector element is exposed to an atmosphere to be measured or a structure in which a gas permeable film which has permeability to the gas is used and in contact with a back channel instead of using the insulating layer 111 having a water-absorbing property may be used. As the gas permeable film, a porous inorganic insulating film or the like can be used, for example.

As described above, two kinds of thin film transistors, that is, the thin film transistor serving as the detector element of the gas sensor and the thin film transistor included in the detection circuit are formed over one substrate by the same process, whereby a gas sensor can be formed at low cost without a complicated manufacturing process.

This embodiment can be combined with any of the other embodiments, as appropriate.

Embodiment 2

In this embodiment, an example of a circuit configuration of a humidity sensor which is one of gas sensors of the present invention will be described.

Figure 3:
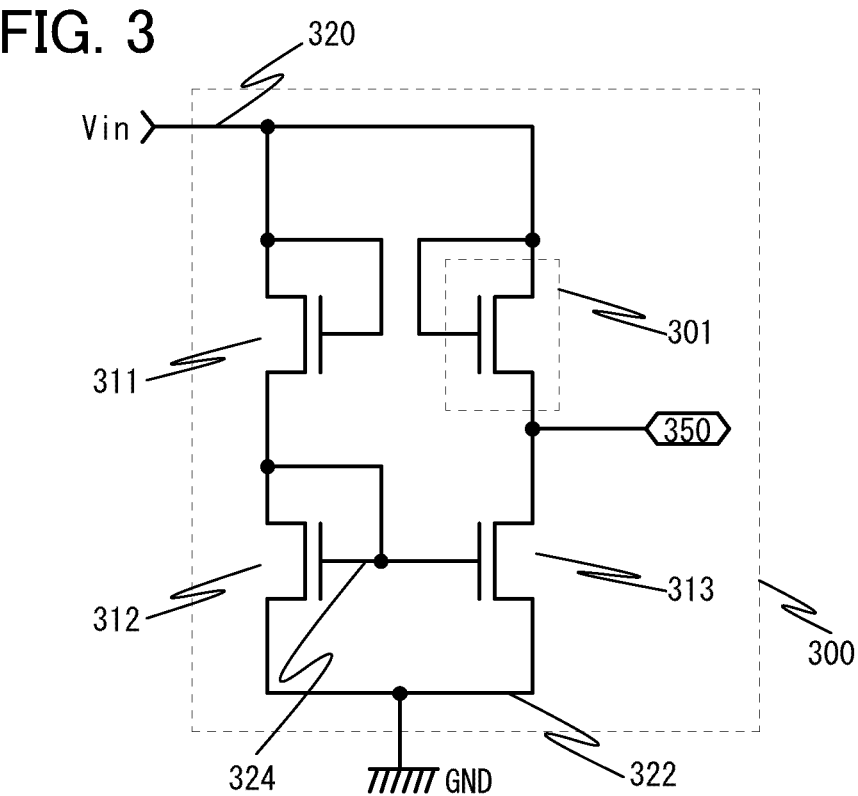
FIG. 3 illustrates a gas sensor according to one embodiment of the present invention.

FIG. 3 is a structure example of a humidity sensor circuit in this embodiment.

A humidity sensor 300 includes a transistor 301, a transistor 311, a transistor 312, and a transistor 313. All of the transistors are n-channel transistors.

A first terminal and a gate electrode of the transistor 311 are connected to a power supply line 320, and a second terminal of the transistor 311 is connected to a first terminal and a gate electrode of the transistor 312. The first terminal and the gate electrode of the transistor 312 are connected to a gate electrode of the transistor 313, and a second terminal of the transistor 312 is connected a ground line 322. A first terminal and a gate electrode of the transistor 301 are connected to the power supply line 320, and a second terminal of the transistor 301 is connected to an output terminal 350 and a first terminal of the transistor 313. A second terminal of the transistor 313 is connected to the ground line 322.

In the humidity sensor 300, the second electrodes of the transistor 312 and the transistor 313 are connected to the ground line 322, the gate electrodes of the transistor 312 and the transistor 313 are connected to each other, and these two transistors form a current mirror circuit.

The transistor 301 is a detector element of a humidity sensor, and a structure which is similar to that of the thin film transistor 101 described in Embodiment 1 is used.

On the other hand, a structure which is similar to that of the thin film transistor 201 described in Embodiment 1 is used for the transistor 311, the transistor 312, and the transistor 313.

Therefore, when the humidity sensor 300 is disposed in an atmosphere to be measured, the threshold voltage of the transistor 301 is decreased in response to the humidity in the atmosphere to be measured. On the other hand, threshold voltage of each of the transistor 311, the transistor 312, and the transistor 313 remains unchanged.

Note that in this embodiment, all of the transistors included in the humidity sensor 300 have the same size.

Next, circuit operation is described. Power source voltage Vin is applied to the power supply line 320 of the humidity sensor 300. The transistor 312 and the transistor 313 form a current mirror circuit; accordingly, when the power source voltage Vin is applied to the power supply line 320, current with the same value flows through the transistor 312 and the transistor 313.

Here, all of the current which flows through the transistor 311 flows through the transistor 312. In addition, all of the current which flows through the transistor 301 flows through the transistor 313. At this time, values of current which flows through the transistor 311 and the transistor 312 are determined by electrical characteristics of the transistor 311 and the transistor 312, respectively. Thus, current which flows through the transistor 301 has always a given value.

Further, the transistor 311 and the transistor 312 have the same size; therefore, a node 324 connected to the gates of the transistor 312 and the transistor 313 always satisfies Vin/2. In other words, a voltage of Vin/2 is always applied to the gate of the transistor 313.

At this time, focusing on the transistor 301, voltage Vgs is applied between the gate and the source (second terminal) of the transistor 301 in accordance with the current which flows through the transistor 311. Here, Vgs is gate-source voltage of a transistor.

Here, the threshold voltage of the transistor 301 is decreased by $\Delta V$ in response to the humidity in the atmosphere to be measured. At this time, the current which flows through the transistor 301 needs to have a given value; therefore, a source potential of the transistor 301, that is, voltage of the output terminal 350 is increased by $\Delta V$ in order to keep the given value.

At this time, although the source-drain voltage of the transistor 313 is decreased by $\Delta V$, constant voltage Vin/2 is applied to the gate of the transistor 313. Therefore, a relation of $|Vgs-Vth| \leq |Vds|$ is always satisfied in the transistor 313, and operation in a saturation region is secured (here, Vth represents threshold voltage of a transistor and Vds represents source-drain voltage of a transistor). Accordingly, even when the voltage of the output terminal 350 is increased by $\Delta V$ and Vds is increased by $\Delta V$, the value of the current which flows through the transistor 313 remains unchanged.

As described above, in the case where the threshold voltage of the transistor 301 serving as the detector element is decreased in response to the humidity in the atmosphere to be measured, voltage corresponding to a change in the threshold voltage is output to the output terminal 350.

When such a humidity sensor is used, a change of the humidity in the atmosphere to be measured can be detected as a change in output voltage.

Note that in this embodiment, the transistor 301 serving as the detector element has the same structure as the thin film transistor 101 described in Embodiment 1; however, this embodiment is not limited to this structure, and a transistor serving as a detector element, such as the thin film transistor 121 or the thin film transistor 141, can be used. Similarly, in this embodiment, the transistor included in the detection circuit has the same structure as the thin film transistor 201 described in Embodiment 1; however, a transistor such as the thin film transistor 221 or the thin film transistor 241, can be used.

Note that in this embodiment, the circuit in FIG. 3 is used as a circuit configuration of a humidity sensor; however, this embodiment is not limited to this structure. Any circuit may be used as long as the circuit only includes n-channel transistors and can detect a change in threshold voltage of a transistor serving as a detector element.

In this embodiment, all of the transistors included in the humidity sensor 300 have the same size; however, the size can be changed as appropriate. For example, when the size of the transistor 301 is increased, an area in contact with the atmosphere to be measured can be increased, whereby detection sensitivity can be improved.

Note that the circuit configuration of the humidity sensor which is one of gas sensors is described in this embodiment; however, the transistor 301 can be replaced with the transistor having a structure which can detect a highly reactive gas described in Embodiment 1, whereby a sensor which detects the gas can be provided.

When such a gas sensor is used, a gas sensor including only n-channel thin film transistors formed by the same process can be formed at low cost without a complicated manufacturing process.

This embodiment can be combined with any of the other embodiments, as appropriate.

Embodiment 3

In this embodiment, a structure example of an RF tag provided with a humidity sensor which is one of gas sensors of the present invention will be described.

Figure 4:
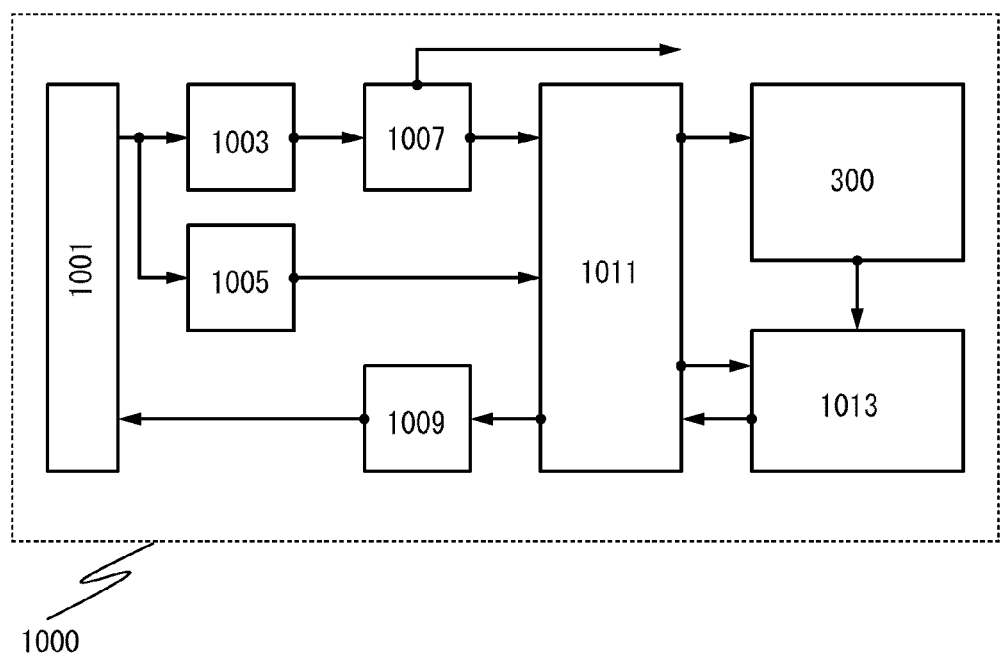
FIG. 4 illustrates an RF tag according to one embodiment of the present invention.

FIG. 4 is a block diagram illustrating one embodiment of the RF tag of the present invention. In FIG. 4, an RF tag 1000 includes an antenna circuit 1001, a rectifier circuit 1003, a demodulation circuit 1005, a regulator 1007, a modulation circuit 1009, a logic circuit 1011, the humidity sensor 300, and a conversion circuit 1013.

An example of the operation of the RF tag 1000 is described. When a radio wave is transmitted from an interrogator, the radio wave is converted into AC voltage in the antenna circuit 1001. In the rectifier circuit 1003, the AC voltage from the antenna circuit 1001 is rectified to generate voltage for power supply. The voltage for power supply, which is generated in the rectifier circuit 1003, is fed to the regulator 1007. The regulator 1007 stabilizes the voltage for power supply, which is generated from the rectifier circuit 1003, or adjusts the level thereof, and supplies the voltage for power supply to the circuits such as the logic circuit 1011, the humidity sensor 300, the conversion circuit 1013, and the modulation circuit 1009.

The demodulation circuit 1005 demodulates an alternating-current signal received by the antenna circuit 1001 to output to the logic circuit 1011 of the next stage. The logic circuit 1011 performs arithmetic processing in accordance with the signal input from the demodulation circuit 1005 to generate another signal. Further, the logic circuit 1011 analyses the signal input from the demodulation circuit 1005, and in accordance with an instruction transmitted from the interrogator, outputs signals to the humidity sensor 300 and the conversion circuit 1013.

The circuit described in Embodiment 2 can be used for the humidity sensor 300. Accordingly, when driving voltage Vin is supplied from the logic circuit 1011, an analog signal dependent on the humidity in the atmosphere to be measured is output.

The conversion circuit 1013 converts the analog signal output from the humidity sensor 300 into a digital signal. The output signal converted into the digital signal by the conversion circuit 1013 is output to the logic circuit 1011.

The logic circuit 1011 analyses the signal input from the conversion circuit 1013 and outputs the result to the modulation circuit 1009. The signal output from the logic circuit 1011 is encoded and transmitted to the modulation circuit 1009. The modulation circuit 1009 modulates a radio wave received by the antenna circuit 1001 in accordance with the signal. The radio wave modulated in the antenna circuit 1001 is received by the interrogator.

In this manner, communication between the RF tag 1000 and the interrogator is performed by modulating a radio wave used as a carrier (a carrier wave). As the carrier, there are radio waves with frequencies of 125 kHz, 13.56 MHz, 950 MHz, and the like, which vary depending on the standard. A modulation method includes various methods such as amplitude modulation, frequency modulation, and phase modulation, depending on the standard; however, any modulation may be employed as long as it is based on the standard.

A transmission method of signals can be classified into an electromagnetic coupling method, an electromagnetic induction method, a micro-wave method, and the like in accordance with a wavelength of the carrier.

In this embodiment, the humidity sensor 300 has the structure described in the above embodiment, a humidity sensor formed at low cost is used, and humidity in an environment where the RF tag 1000 is disposed can be measured wirelessly without leading of a connection wiring.

Part of the circuit included in the RF tag 1000 may be formed using the thin film transistor 201 described in Embodiment 1. A semiconductor layer of the thin film transistor 201 includes an oxide semiconductor; therefore, off-state current of the thin film transistor 201 is significantly low. Accordingly, the thin film transistor 201 is used for part of the circuit included in the RF tag 1000, whereby consumption current of the circuit can be suppressed without increase in manufacturing steps; as a result, power consumption of the RF tag 1000 can be reduced.

In this embodiment, the structure of the RF tag 1000 including the antenna circuit 1001 is described; however, the RF tag according to one embodiment of the present invention does not necessarily include an antenna circuit. In addition, the RF tag illustrated in FIG. 4 may be provided with an oscillation circuit or a secondary battery.

Note that although the structure of the RF tag including a humidity sensor which is used for a sensor is described in this embodiment, a sensor which detects a highly reactive gas as described in Embodiment 1 can be included.

This embodiment can be combined with any of the other embodiments, as appropriate.

Example 1

In this example, a thin film transistor serving as a detector element of a humidity sensor which is one of gas sensors according to one embodiment of the present invention is formed and the results of electrical characterization evaluation are shown.

A 100-nm-thick silicon nitride film was formed by a plasma-enhanced CVD method and a 150-nm-thick silicon oxynitride film was formed consecutively over a glass substrate to form a base film, and a 100-nm-thick tungsten film was formed as a gate electrode layer over the silicon oxynitride film by a sputtering method. The tungsten film was etched selectively, thereby forming the gate electrode layer.

Then, a 100-nm-thick silicon oxynitride film was formed as a gate insulating film over the gate electrode layer by a plasma-enhanced CVD method.

Next, a 30-nm-thick oxide semiconductor film was formed over the gate insulating film by a sputtering method using an In—Ga—Zn—O-based oxide semiconductor target ($In_2O_3$:$Ga_2O_3$:$ZnO$=1:1:1) under an atmosphere containing argon and oxygen (argon:oxygen=50 sccm:50 sccm) at 200° C. under the following conditions: the distance between the substrate and the target was 80 mm, the pressure was 0.4 Pa, and the direct current (DC) power was 5 kW. Here, an island-shaped oxide semiconductor layer was formed by selectively etching the oxide semiconductor film.

Next, heat treatment was performed at 350° C. under an air atmosphere for one hour.

Next, as a source electrode layer and a drain electrode layer, a titanium film (with a thickness of 100 nm), an aluminum film (with a thickness of 400 nm), and a titanium film (with a thickness of 100 nm) were stacked over the oxide semiconductor film by a sputtering method at 100° C. Here, the source and drain electrode layers were selectively etched so that the channel length L and the channel width W of the transistor were 20 μm and 20 μm, respectively.

Next, a polyimide film was formed as an insulating layer having a water-absorbing property. The polyimide film was formed in such a way that a photosensitive polyimide resin was formed to have a thickness of 1.5 μm by a spin coating method, the photosensitive polyimide resin was selectively exposed to light and development is performed, an opening portion was formed over the gate electrode layer, the source electrode layer, and the drain electrode layer, and heat treatment was performed at 350° C. in an air atmosphere for 1 hour in order to cure the photosensitive polyimide resin.

Through the above process, a transistor having the channel length L of 20 μm and the channel width W of 20 μm was manufactured over the glass substrate.

Next, humidity environment of the transistor of this example was changed and results of electrical characterization evaluation will be described.

In order to measure initial characteristics of the formed transistor, a change in characteristics of the source-drain current (hereinafter, referred to as the drain current), that is, ID-VG characteristics were measured under conditions that the source-drain voltage (hereinafter, the drain voltage) was set to 1 V and 10 V, and the source-gate voltage (hereinafter, the gate voltage) was changed from −20 V to +20 V at room temperature under normal humidity.

Next, the substrate provided with the above-described transistor was preserved in a constant temperature bath for 60 hours under the following condition: at a temperature of 85° C. and a humidity of 85%.

After the substrate was taken out of the constant temperature bath, the substrate was cooled to room temperature, and ID-VG characteristics were measured under the condition which is similar to that of the initial characteristics at room temperature under normal humidity.

Then, baking treatment was performed with a hot plate at 150° C. for 1 hour in order to dry the substrate.

Then, the substrate was taken out of the hot plate and cooled to room temperature, and ID-VG characteristics were measured in a manner similar to that of the initial characteristics at room temperature under normal humidity.

Figure 5:
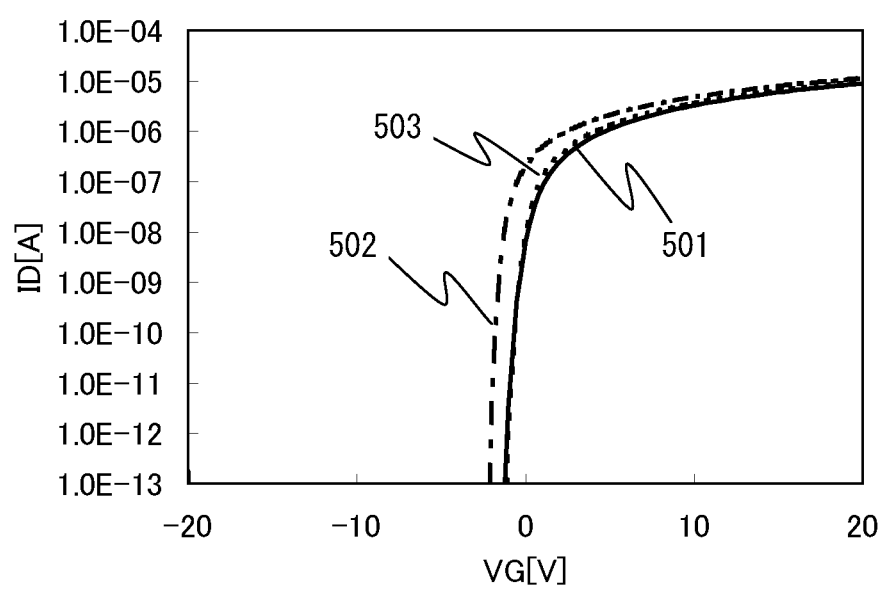
FIG. 5 shows ID-VG characteristics according to one example of the present invention.

FIG. 5 shows measured ID-VG characteristics. In FIG. 5, the horizontal axis represents the gate voltage (VG), and the vertical axis represents the drain current (ID) which is shown with a logarithmic scale.

A solid line 501 in FIG. 5 shows the initial ID-VG characteristics of the transistor, and a chain line 502 shows ID-VG characteristics after preservation at a temperature of 85° C. and a humidity of 85%. In addition, a dotted line 503 shows ID-VG characteristics when the substrate was dried after the preservation.

In those measurements of the ID-VG characteristics of the transistor of this example, the Id became less than or equal to the detection limit of the measurement device in an off region (a region where Vg is from about 0 V to a negative value in most n-channel transistors). Therefore, FIG. 5 does not show a part in which the Id is less than or equal to the detection limit of the measurement device.

As shown by the chain line 502 in FIG. 5, which shows characteristics after preservation in an environment with a humidity of 85%, threshold voltage is shifted to a negative direction by 2.00 V from that in the initial characteristics shown by the solid line 501. In addition, characteristics after the substrate was dried after the preservation, which are shown by the dotted line 503, is shifted to a positive direction by 1.72 V from the characteristics shown by the chain line 502 and is close to a value of the initial characteristics.

As described above, it is confirmed that the threshold voltage of the transistor of this example shifts to a negative side because of humidity, a voltage change is reversible, and the transistor of this example can be used as a detector element of a humidity sensor.

Example 2

In this example, results of calculating input-output characteristics using the circuit described in Embodiment 2 will be shown.

The input-output characteristics of the circuit having the structure illustrated in FIG. 3 were calculated.

In this example, calculation was performed, assuming that sizes of each of the transistor 301, the transistor 311, the transistor 312, and the transistor 313 included in the sensor circuit in FIG. 3, such as the channel length L and the channel width W, were equal to each other. For the calculation, the subthreshold swing (S value) of each of the transistors was set to 100 mV/decade. Further in this example, calculation was performed, assuming that the threshold voltage (hereinafter referred to as Vth) of each of the transistor 311, the transistor 312, and the transistor 313 was 1.6 V. In addition, Vth of the transistor 301 serving as the detector element was changed to the lower voltage side from 1.6 V.

As for the input-output characteristics, voltage output to the output terminal 350 in the case where voltage of the power supply line 320 was changed from 0 V to 10 V was calculated. Further, Vth of the transistor 301 at that time was changed from 1.6 V to −0.4 V.

Figure 6A:
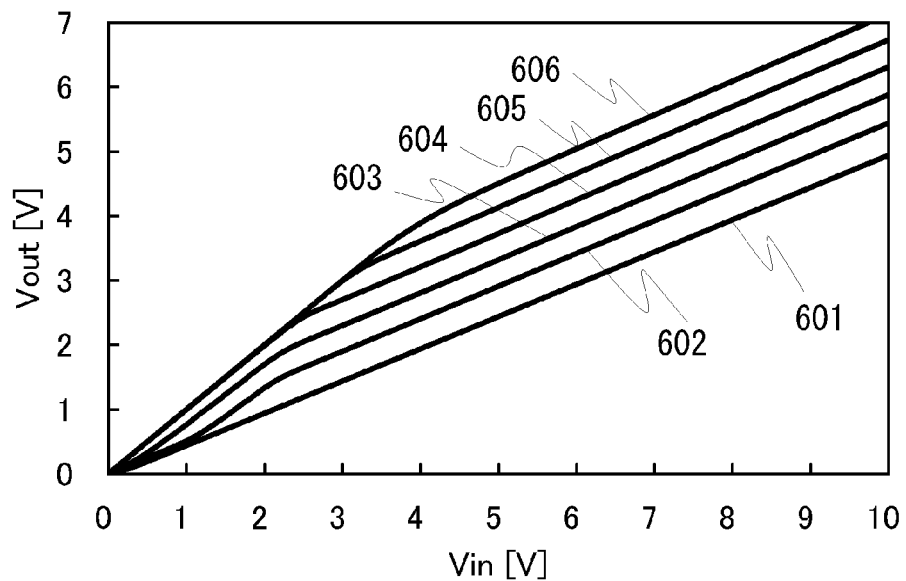
FIGS. 6A and 6B show input and output characteristics according to one example of the present invention.

FIG. 6A shows calculation results. In FIG. 6A, the horizontal axis represents voltage Vin of the power supply line, and the vertical axis represents voltage Vout of the output terminal 350 with respect to Vin.

In FIG. 6A, reference numerals 601 to 606 denote output voltage Vout with respect to the power source voltage Vin when Vth of the transistor 301 was changed by every −0.4 V from 1.6V to −0.4 V. As the voltage Vth of the transistor 301 is decreased, Vout is increased.

Figure 6B:
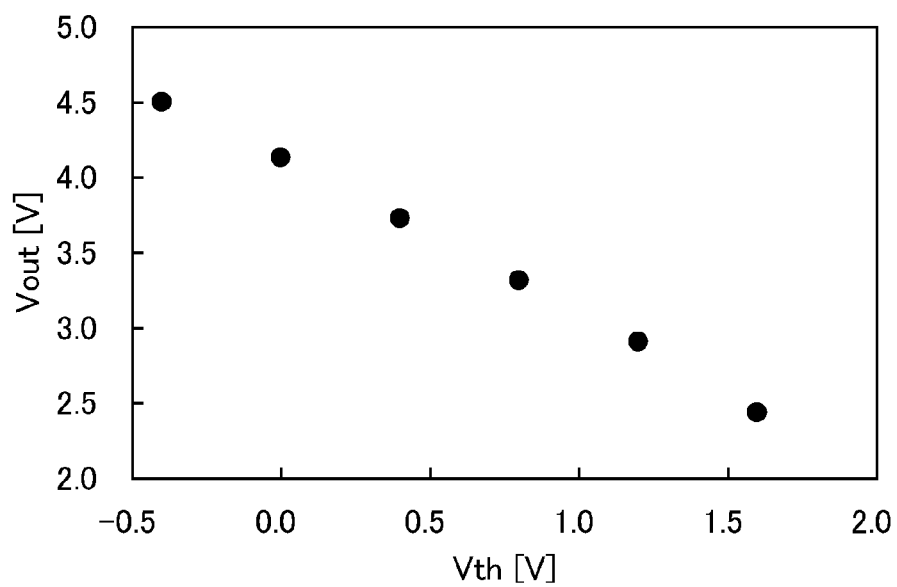

FIG. 6B is a graph in which Vout in the case of Vin=5 V in FIG. 6A is plotted with respect to Vth of the transistor 301. The horizontal axis represents Vth of the transistor 301, and the vertical axis represents the output voltage Vout with respect to Vth of the transistor 301.

It is confirmed from FIG. 6B that the output voltage Vout is changed almost linearly with respect to Vth when Vin is set to 5 V.

As described above, it is confirmed that a change of the threshold voltage of the transistor serving as the detector element can be detected as a change of the output voltage and the transistor serving as the detector element in combination with a transistor as described in Example 1 serves as a gas sensor in the sensor circuit of this example.

This application is based on Japanese Patent Application serial no. 2010-133916 filed with the Japan Patent Office on Jun. 11, 2010, the entire contents of which are hereby incorporated by reference.

What is claimed is:

1. A gas sensor comprising:
a detection portion including a first transistor and a circuit portion including a second transistor over one insulating surface,
wherein the first transistor comprises:
 a first gate electrode layer over the insulating surface;
 a gate insulating layer over the first gate electrode layer;
 a first oxide semiconductor layer, one surface of which is in contact with the gate insulating layer and the other surface of which is in contact with an atmosphere; and
 a first source electrode layer and a first drain electrode layer that are in contact with the first oxide semiconductor layer, and
wherein the second transistor comprises:
 a second gate electrode layer over the insulating surface;
 the gate insulating layer over the second gate electrode layer;
 a second oxide semiconductor layer, one surface of which is in contact with the gate insulating layer and the other surface of which is in contact with a protective insulating layer; and
 a second source electrode layer and a second drain electrode layer that are in contact with the second oxide semiconductor layer.

2. The gas sensor according to claim 1, wherein an insulating layer including a gas permeable property is in contact with the atmosphere and provided between the first oxide semiconductor layer and the atmosphere.

3. The gas sensor according to claim 1, wherein the first oxide semiconductor layer and the second oxide semiconductor layer are formed of the same material.

4. The gas sensor according to claim 1, wherein the first oxide semiconductor layer and the second oxide semiconductor layer are formed from the same layer.

5. A gas sensor comprising:
a detection portion including a first transistor and a circuit portion including a second transistor over one insulating surface,
wherein the first transistor comprises:
 a first gate electrode layer over the insulating surface;
 a gate insulating layer over the first gate electrode layer;
 a first oxide semiconductor layer, one surface of which is in contact with the gate insulating layer and the other surface of which is in contact with an atmosphere, the first oxide semiconductor layer overlapping with the first gate electrode layer; and
 a first source electrode layer and a first drain electrode layer that are in contact with the first oxide semiconductor layer, the first source electrode layer and the first drain electrode layer overlapping with the first gate electrode layer, and
wherein the second transistor comprises:
 a second gate electrode layer over the insulating surface;
 the gate insulating layer over the second gate electrode layer;
 a second oxide semiconductor layer, one surface of which is in contact with the gate insulating layer and the other surface of which is in contact with a protective insulating layer, the second oxide semiconductor layer overlapping with the second gate electrode layer; and
 a second source electrode layer and a second drain electrode layer that are in contact with the second oxide semiconductor layer, the second source electrode layer and the second drain electrode layer overlapping with the second gate electrode layer.

6. The gas sensor according to claim 5, wherein an insulating layer including a gas permeable property is in contact with the atmosphere and provided between the first oxide semiconductor layer and the atmosphere.

7. The gas sensor according to claim 5, wherein the first oxide semiconductor layer and the second oxide semiconductor layer are formed of the same material.

8. The gas sensor according to claim 5, wherein the first oxide semiconductor layer and the second oxide semiconductor layer are formed from the same layer.

* * * * *